United States Patent [19]

Li et al.

[11] 4,174,342

[45] Nov. 13, 1979

[54] N-(ACENAPHTHENYL)MALEIMIDES

[75] Inventors: Jorge P. Li, Libertyville; Frank C. Becker, Gurnee, both of Ill.

[73] Assignee: Abbott Laboratories, North Chicago, Ill.

[21] Appl. No.: 890,736

[22] Filed: Mar. 27, 1978

[51] Int. Cl.$^2$ .................. C07D 207/40; A61K 31/40; C08L 33/00

[52] U.S. Cl. ........................ 260/45.8 N; 260/326.5 C; 106/15.05

[58] Field of Search .................... 260/326.5 C, 45.8 N; 424/274; 106/15 FP

[56] References Cited

U.S. PATENT DOCUMENTS 3,004,036  10/1961  Fan et al. ...................... 260/326.5 C

*Primary Examiner*—Jose Tovar
*Attorney, Agent, or Firm*—Paul D. Burgauer; Robert L. Niblack

[57] ABSTRACT

By the addition of a relatively small amount of N-(acenaphthenyl)maleimides carrying optional substituents, synthetic films, plastics, woven or knitted synthetic or cellulosic fabrics, or paint can be protected against fungal and bacterial deterioration.

10 Claims, No Drawings

N-(ACENAPHTHENYL)MALEIMIDES

DETAILED DESCRIPTION OF THE INVENTION

Synthetic, film-forming materials, such as those used in the manufacture of plastic films or woven fabrics made from synthetic or cellulosic fibers are known to be subject to bacterial or fungal attacks. This is particularly known to those manufacturers whose products will be used on exterior surfaces and/or under conditions that are prone to hose undesirable fungal and bacterial microorganisms.

In order to prevent bacterial or fungal attack and consequent deterioration of the polymeric or cellulosic material so attacked or the substrate to which they are applied, manufacturers of plastic films or paints or woven fabrics have used a number of biocides on a routine basis. Many of the currently used industrial biocides are arsenicals; they are highly successful in preventing bacterial or fungal deterioration of paints and plastics. For environmental reasons, however, arsenicals are now less accepted in some of the industrial uses where biocides are needed. It has thus become highly desirable to find new, nonarsenical biocides that provide protection for polymeric substrates of all types, including film-formers, plastics, cellulosics and the like.

It has now been found that a cellulosic, plastic or film-forming polymeric composition, knitted, woven, molded or extruded into a continuous form can be protected against fungal attacks when they contain or are coated with between 0.005 and 5.0% by weight of a compound of the formula:

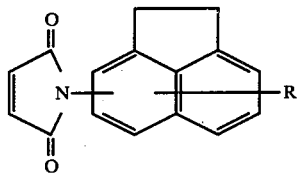

I.

wherein R is hydrogen or nitro. The new compounds have been found to be potent industrial fungicides when added to the above-named substrates.

In many instances, the compounds of Formula I also inhibit the growth of bacteria or fungi in contact with the surface of the object made from a polymeric or cellulosic material containing it, particularly when said compounds are present in the higher range of the concentration recited above. In the case of a coating formulation including certain paints containing the above compound, the substrate to which it is applied is also protected.

For the purpose of the present description, the term "film-forming" should be understood to refer to the polymeric particles, whether those particles are present as dry, particulate matter or in a liquid, dissolved, suspended, coherent, continuous or any other form, particularly including the ultimate form for which those particles are designed. The term "plastic" is used in a similarly broad version and is to be understood to include those polymeric materials which can be extruded, injection- or compression- molded into the desired ultimate shape. The term "cellulosic" is primarily designed to refer to cotton, but also includes those cellulosic derivatives wherein the basic cellulosic structure of the fibrous material has undergone such chemical modifications that does not materially change the number of repeating units in the cellulose structure. The current process and composition will be particularly useful in fabrics made from cellulosic or olefin polymers, knitted or woven into structures exposed to outdoor conditions, such as outdoor-wear, tents, tarpaulins and the like.

The effect of the present invention is best understood by reference to a general embodiment: to a film-forming mixture containing a synthetic polymeric material which is to be processed into a continuous phase and contains the usual ingredients, such as dyes, pigments, plasticizers, preservatives, and the like is added between 0.005 and 5.0% by weight of the compound of formula I and all ingredients are dispersed to form a homogeneous mass. Such a mixture is stable under normal storage conditions; it can be stored for extended periods of time under conditions usually required for such materials. A film or plastic article including a coating made with this mixture is then resistant to fungal or bacterial attack. This is the case whether said particle is obtained by compression-molding, injection-molding, extrusion or whether it is a film such as obtained with a paint formulation by brushing, spray-coating or dip-coating it onto the substrate and subsequent drying. Dip-coating is primarily applicable where the continuous substrate is a woven or knitted cellulosic material or where small objects are to be covered on all sides by the paint formulation. In most instances, the substrate and areas in contact therewith are also protected from deterioration by bacterial or fungal attack.

In order to illustrate the effect of the addition of the compound of formula I to a film-forming or plastic mixture or a woven fabric, and the manufacture of these compounds, reference is made to the following examples which, however, are not intended to limit the invention in any respect.

EXAMPLE 1

5-Nitroacenaphthene is made by nitrating acenaphthene with nitric acid in the presence of acetic acid according to the method of Rowe and Davies, J. Chem. Soc. 117, 1346 (1920). Standard reduction methods using tin or stannous chloride in hydrochloric acid or by using Raney nickel with ethanol or hydrazine produces 5-aminoacenaphthene.

To a solution of 12.9 g. of 5-aminoacenaphthene in 60 ml. of glacial acetic acid is added 8.5 g. of powdered maleic anhydride with stirring. A yellowish brown paste forms in this mildly exothermic reaction. The mixture is then heated to reflux for 4 hours, cooled and filtered. The filtrate is evaporated in vacuo and the residue is triturated with cold water. The solid product is collected and air-dried, producing 18.5 g. of N-(5-acenaphthenyl)maleimide, melting at 178°-9° C. after recrystallization from ethanol.

EXAMPLE 2

5-Acetyl-acenaphthene is prepared by acetylating acenaphthene according to Nightingale et al., J. Am. Chem. Soc., 67, 1263 (1945), which is then nitrated by the method of Richter, J. Org. Chem. 21, 619 (1956) to produce 5-Acetyl 6-nitroacenaphthene. A Beckmann rearrangement followed by the hydrolysis described by Richter (doc. cit.) produces 6-nitro-5-acenaphthenylamine. Heating the latter with an equimolar amount or an excess of maleic anhydride in accordance with Example 1 produces N-(6-nitro-5-acenaphthenyl)maleimide which, however, requires column chromatography over silica gel for purification; it melts at 220°-2° C.

When replacing the above 5-aminoacenaphthene carrying an optional nitro group by a corresponding 3- [Friedman, et al, J. Am. Chem. Soc., 71, 3010 (1949)] or 4-aminoacenaphthene [Morgan et al, J. Soc. Chem. Ind., 49, 413T (1930)], the corresponding maleimides are obtained in fashion described in this or the preceding Example.

EXAMPLE 3

In a minimum inhibitory concentration (MIC) test, the amount of the test compound needed to prevent funal growth is established. In this test, potato dextrose agar containing the test compound at a specified concentration is inoculated with 1 ml. of a broth containing 10,000 units each of *A. niger* and *P. funiculosum*. The agar plates inoculated in this fashion are incubated at 30° C. for 2 weeks and growth of the microorganisms is rated on a scale of 0 to 4 with 0 indicating no growth whatsoever and 4 indicating uninhibited growth.

The compound described in Example 1 shows 0 at 100 ppm and 4 at 10 ppm; the compound described in Example 2 shows 0 at 100 ppm and 3 at 10 ppm.

EXAMPLE 4

Water: 250 parts
Anionic surfactant: 8 parts
Non-ionic surfactant: 2.5 parts
Tetrapotassium phosphonate: 1 part
Hydroxyethylcellulose: 2.5 parts
Ethylene glycol: 25 parts
Cellulose acetate: 15 parts
Defoamer: 3 parts
Titanium dioxide: 175 parts
Magnesium silicate: 250 parts
Fungicide of structure I (R=4): 5 lbs/100 gals.

The above ingredients are dispersed for 20 minutes and then blended with 400 parts of a vinyl-acrylic emulsion (sold as UCAR-365 by Union Carbide) and 1 part of a defoamer.

After the paint is dried, the painted surface is inoculated with a mixture of *A. pullulans, P. funiculosum* and *A. niger,* containing 10,000 spores/ml. of each. The samples are then placed in a mold box for a period of 4 weeks at 30° C. and 90%-100% relative humidity. The results of the paint samples with the current fungicide and a control (no fungicide) sample are rated on a scale of 0-4 wherein 0 stands for no fungal growth on the sample, 1 for 0-25% growth, 2 for 25-50% growth, 3 for 50-75% growth and 4 for 74-100% growth of spores over the painted surface.

After 4 weeks, the control sample shows a growth rating of 4, 4 and 3 on three samples; the above paint containing the new fungicide shows a rating of 1, 1 and 0.5 on three specimens.

While the above general antifungal tests and the specific paint protection test is only shown for the compounds of formula I wherein the maleimide function is in the 5-position of the acenaphthene or 6-nitroacenaphthene moiety, similarly good results are obtained when the N-(4-nitro-5-acenaphthenyl)-, the N-(5-nitro-4-acenaphthenyl)-, the N-(4-acenaphthenyl)-, the N-(3-acenaphthenyl)-, the N-(4-nitro-3-acenaphthenyl)-, the N-(3-nitro-7-acenaphthenyl)-, the N-(3nitro-8-acenaphthenyl)-, the N-(6-nitro-3-acenaphthenyl)-maleimides or the other 11 isomers are used at a level of 2-9 lbs. per 100 gals. of paint. Also, similar MIC results are obtained with these position isomers.

The above examples only show the use of the new fungicide in a particular paint composition. However, they can also be used in other film formulation, resinous plastics on cellulosic or synthetic fibers and fibers made therefrom. In these instances, the fabrics are dipped in a solution containing the compound of formula I in such a fashion that between 0.2 and 1% of the new fungicide remains on said fabric. In the case of extruded or molded plastic or resinous films, the new fungicide is incorporated into the mix prior to extrusion or molding at a concentration of 0.1 to 1%). In both of these instances, other materials in close contact with the treated fabric or film are often protected also. This observation is particularly important for paint films were the paint surface also becomes protected against fungal growth.

We claim:

1. A plastic, cellulosic or other film-forming composition resistant to fungal attack comprising said plastic cellulosic or film-forming composition and between 0.005 and 5.0% by weight of an acenaphthene derivative of the formula

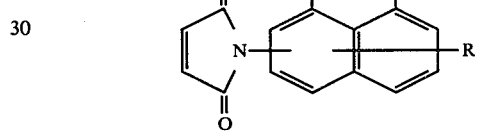

wherein R is H or NO₂.

2. The composition of claim 1 wherein said acenaphthene derivative is the N-(5-acenaphthenyl)maleimide.

3. The composition of claim 1 wherein R is nitro.

4. The composition of claim 1 wherein R is a nitro group attached to the 6- position.

5. The composition of claim 1 wherein said acenaphthene derivative is the N-(6-nitro-5-acenaphthenyl)-maleimide.

6. A compound of the formula

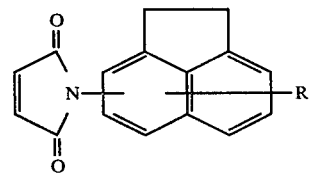

wherein R is H or NO₂.

7. A compound of claim 6 wherein R is H.

8. The compound of claim 7 wherein said acenaphthene moiety is attached to the nitrogen at its 5- position.

9. A compound according to claim 6 wherein R is NO₂.

10. The compound of claim 9 wherein said acenaphthene moiety is attached to the nitrogen through its 5- position and the nitro group is in the 6- position.

* * * * *